United States Patent

Toth

[11] Patent Number: 5,989,922
[45] Date of Patent: Nov. 23, 1999

[54] METHOD FOR DETERMINING RHEUMATOID FACTORS AND AGENTS FOR CARRYING OUT THE METHOD

[75] Inventor: Tibor Toth, Marburg, Germany

[73] Assignee: Behring Diagnotics GmbH, Marburg, Germany

[21] Appl. No.: 08/310,042

[22] Filed: Sep. 22, 1994

Related U.S. Application Data

[63] Continuation of application No. 08/140,712, Oct. 22, 1993, abandoned, which is a continuation of application No. 08/010,326, Jan. 28, 1993, abandoned.

[30] Foreign Application Priority Data

Feb. 1, 1992 [DE] Germany .............................. 42 02 924

[51] Int. Cl.$^6$ .................................................. G01N 33/546
[52] U.S. Cl. .......................... 436/507; 436/509; 436/518; 436/531; 436/533; 436/534; 436/536; 436/811; 530/391.1; 530/812
[58] Field of Search .................................... 436/507, 509, 436/518, 531, 533, 536, 811, 534; 530/812, 391.1

[56] References Cited

U.S. PATENT DOCUMENTS

| | | |
|---|---|---|
| 4,292,038 | 9/1981 | Kondo et al. . |
| 4,547,466 | 10/1985 | Turanchik et al. ...................... 436/509 |
| 4,569,919 | 2/1986 | Toth et al. .............................. 436/533 |
| 4,590,156 | 5/1986 | Dorsett . |
| 4,600,698 | 7/1986 | Toth ........................................ 436/534 |
| 4,670,381 | 6/1987 | Frickey et al. .............................. 435/7 |
| 4,935,339 | 6/1990 | Zahradnik .................................... 435/5 |

FOREIGN PATENT DOCUMENTS

| | | |
|---|---|---|
| 29 18 342 | 11/1980 | Germany . |
| 63-235868 | 1/1989 | Japan . |
| 2259569 | 1/1991 | Japan . |

OTHER PUBLICATIONS

Genung and Hsu, "Immobilization of Immunoglobulins on Polystyrene Latex Beads—Characterization by Density Gradient Centrifugation", Biotech and Bioeng., 20:1129–1141 (1978).
Latex Coating, Estapor Microspheres News, Jan. 1996, at 4.
Sorensen and Brobeck, "Assessment of Coating–Efficiency in ELISA plates by Direct Protein Determination", J. Immun. Meth., 95:291–93 (1986).
Daniel P. Stites, MD, "Clinical Laboratory Methods for Detection of Antigens and Antibodies," Chapter 26 in *Basic and Clinical Immunology*, Fudenberg et al., eds., Lange Medical Publications, Los Altos, California, p. 363, (1980).
"Nephelometric Assay of Antigens and Antibodies with Latex Particles", J. Grange et al., Journal of Immunological Methods, 18:365–375 (1977).

*Primary Examiner*—Christopher L. Chin
*Attorney, Agent, or Firm*—Finnegan, Henderson, Farabow, Garrett & Dunner, L.L.P.

[57] ABSTRACT

The invention relates to an immunochemical method for the detection and determination of rheumatoid factors using immune complexes as specific binding partners as well as to the preparation of reagents that are suitable for these methods.

15 Claims, No Drawings

METHOD FOR DETERMINING RHEUMATOID FACTORS AND AGENTS FOR CARRYING OUT THE METHOD

This application is a continuation of application Ser. No. 08/140,712, filed Oct. 22, 1993, which is a continuation of application Ser. No. 08/010,326 filed Jan. 28, 1993, now abandoned.

The invention relates to an immunochemical method for the detection and determination of rheumatoid factors using immune complexes as specific binding partners as well as to the preparation of reagents that are suitable for these methods.

Serologic investigation methods have found wide application in rheumatologic diagnosis. In these methods, sera are examined for the presence of antibodies which, in the event of these illnesses, the body forms against endogenous substances; these antibodies are therefore also termed "autoantibodies".

In rheumatoid diagnosis two groups of autoantibodies have in particular proved to be important: rheumatoid factors (RF) and anti-nuclear antibodies (ANA). Rheumatoid factors are antibodies against endogenous immunoglobulins, i.e. anti-immunoglobulin antibodies, and antinuclear antibodies are antibodies against structures in endogenous cell nuclei. Rheumatoid factors are found in all the immunoglobulin classes; they belong mainly to the immunoglobulin classes IgM, IgG and IgA.

Known test methods for the detection of rheumatoid factors are based on the agglutination of erythrocytes or latex particles, for example, which are coated with human or animal IgG. These methods permit only qualitative or semiquantitative determination of rheumatoid factors and the reading of the results of this agglutination test is, as a consequence of the visual evaluation, subjective. Used besides agglutination methods (latex agglutination, Waaler-Rose test), radioimmunoassays and enzyme immunoassays, for determining rheumatoid factors are nephelometric or turbidimetric methods. Light scattering and, consequently, the sensitivity of the nephelometric or turbidimetric method is dependent on the "particle size" of the antigen or antibody. A known method comprises the binding of a human immunoglobulin to latex particles, which themselves scatter the light.

As well as quantitative evaluation, radioimmunoassay and enzyme immunoassay methods also permit a differentiation of the rheumatoid factor classes IgM, IgG and IgA. They are, however, very labor-intensive and the determination takes several hours.

As is evident from the work of J. Grange and coworkers in J. Immunol. Meth. 18 (1977) 365–375, the scattered light signal decreases initially during the titration with antigen of an antibody bound to latex, because with increasing agglutination the particle number decreases. Subsequently a further increase in antigen concentration causes the aggregate size to increase, resulting in an increase in scattered light intensity, until the scattered light signal decreases once more as the antigen quantity rises further to the level of antigen excess. It is important, for the quantitative test, to regulate the agglutination conditions of the latex in such a way that, in a titration of latex-bound antibodies with antigen, or of latex-bound antigen with antibodies, the increase in agglutination can, as far as possible, be measured as an increase in scattered light intensity over a wide range.

In carrying out the particle-boosted agglutination tests for the determination of rheumatoid factors, serial dilutions of the sera must first of all be made. Disadvantages are ambiguous changes the scattered light intensity in the titration, a very narrow measurement range, i.e. a steep rise in the standard curve, as well as high blank values of the latex reagent. It has been proposed, inter alia, (German Offen- legungsschrift DE 29 18 342), that latex particles of two different size ranges should be mixed in order to extend the measurement range. Additionally, these latex par- ticles of different size ranges are loaded on each occasion with at least one quantity of antibodies which is different from the other. Disadvantages are the incubation time of up to 1 hour, as well as the measure- ment of light scattering after a further 15 min in the laser nephelometer. Recently, further, in some cases automated, methods for determining rheumatoid factors have been described, but are also unable to solve the problems such as dilution consistency, high sensitivity and wide ranges for measurement.

It has now been found, surprisingly, that these difficulties can be removed if, instead of human gamma globulin, an immune complex composed of antibodies against human IgG from sheep and human IgG or an immune complex composed of antibodies against human gamma globulin from rabbit and human gamma globulin are used. The immune complexes are bound to latex particles according to known methods. The latex reagent that is obtained can be used in the manual latex agglutination test or in the nephelometric or turbidimetric methods, employing kinetic or end-point methods.

The invention accordingly relates to an immunochemical method for the detection and determination of rheumatoid factors (analyte) by means of a specific binding partner, wherein the latter is an immune complex.

Preferred in this connection is a method wherein the immune complex has been prepared from antisera from animals immunized with an antigen of human, animal or vegetable origin that is not the analyte. Particularly preferred is a method in which the antibody:antigen ratio in the immune complex is 1:0.05 to 5.

Very particularly preferred is a method in which the immune complex is bound to a solid phase.

Preferably an antiserum from sheep or rabbit is used.

Further preferred is a method as described above, wherein the evaluation takes place using a particle-boosted immunological method.

The invention further relates to a process for the preparation of an immune complex for use in the above-described method, wherein the immune complex is prepared in an aqueous solution in the presence of up to 50% by volume of a cyclic amide, preferably in the presence of γ-amino-butyrolactam.

The latex particles can be loaded by adsorption or by covalent bonding of proteins. Latex derivatives with free carboxyl groups, amino groups, aldehyde groups and epoxy groups as well as vicinal hydroxyl groups can be employed for the covalent bonding.

In many cases, binding of proteins to the latex by adsorption was found to be the most favorable.

Methods of loading latex particles with proteins and/or peptides are known to the person skilled in the art.

The latices that can be used for preparing the reagent according to the invention can be obtained, for example, by polymerizing olefinically unsaturated monomers. Preferred are styrene copolymers, such as styrene-butadiene copolymers and acrylonitrile-butadiene-styrene copolymers, vinyl acetate-acrylate copolymers or vinyl chloride-acrylate copolymers.

Polystyrene latex suspensions or emulsions of suitable particle size (50–500 nm) can also be obtained under various trade names from a number of manufacturers. Monodisperse and polydisperse latex suspensions are suitable.

The immune complexes can be prepared according to known processes by mixing the antigen with the specific anti-body. Suitable for this are specific antisera, gamma globulin fractions from antisera, antibodies purified by immuno-adsorption or monoclonal antibodies. Sera and gamma globulin fractions from antisera, which already contain immune complexes as a result of the immunization of animals, are also suitable. Examples of immune complexes are human-IgG/antiserum against human IgG from sheep, human gamma globulin/antiserum against human gamma globulin from rabbit. The ratio of antibody/antigen in the immune complex depends on the antibody content and amounts to 1:0.05–5, preferably 1:0.5–2, particularly preferably about 1:0.1.

The invention therefore relates also to a process for the preparation of the immune complexes used in the method. Since in the case of the particle-boosted agglutination method a precipitating agent, such as polyethylene glycol (PEG), is generally used, the complexes must not be precipitated by the precipitating agent. Furthermore they must be stable on storage for a relatively long period, that is as a rule at least 3 months, preferably at least 12 months.

The preparation of the complex takes place in an aqueous solution, preferably in the presence of a polar solvent that is readily miscible with water, such as dimethyl sulfoxide or dimethylformamide. Preferred is the preparation of the complexes in the presence of a cyclic amide, pyrrolidone (γ-aminobutyrolactam) being particularly suitable. The immune complexes thus prepared are stable on storage in aqueous solutions for at least 3, preferably at least 12 months.

Loading the latex particles with the immune complex can be carried out by a method known to the person skilled in the art. The loading can, for example, take place as follows:

An immune complex prepared from an antiserum/antigen is mixed with a suspension of the latex particles with a concentration of about 50 to 200, preferably 100 g/l, and incubated for 0.5 to 5 hours at a temperature of between 0 and +60 °C, preferably +20–+60° C.

The portion of the immune complex which is not bound to the latex particles can be removed by centrifugation and resuspension of the solid material. For use, the reagent can be resuspended in a buffer solution, preferably glycine-NaCl buffer of pH 7–8.5, which, if required, can be mixed with a protein, for example with human albumin or bovine albumin.

According to another method for loading the latex particles, the immune complex is taken up in a glycine-NaCl buffer, stabilized if required with human or bovine albumin, and mixed with a 0.5 to 2% polystyrene-latex suspension until the required sensitivity is reached. The reagent thus prepared can be stored at +4° C or lyophilized.

The antisera which can be used for preparing the antibody are obtained by immunizing animals, in particular rabbits, sheep and goats, with proteins of human, animal or vegetable origin. Examples are: anti-human IgG serum from rabbit, anti-human gamma globulin from rabbit, anti-rabbit gamma globulin serum from sheep, anti-human IgG serum from sheep.

Particularly suitable are the anti-human IgG serum from sheep and anti-human gamma globulin serum from rabbit. The immunization was carried out according to known methods. The immunization dose and time depend on the immunogenicity and the molecular weight of the protein.

Monoclonal antibodies can also be employed as antibodies for the purpose of this invention.

The following examples illustrate the method according to the invention:

EXAMPLE 1

A) Preparation of the immune complex 56 ml of (16 g/l) human gamma globulin solution in isotonic sodium chloride solution are added, while stirring vigorously, to 25 ml of antiserum against human gamma globulin and 25 ml of isotonic sodium chloride solution. The solution was subsequently incubated for 5 hours. at +56° C and mixed with 5 ml of pyrrolidone.

B) Preparation of the latex reagent 6 ml of immune complex and 450 ml of (10 g/l) of polystyrene latex were used. For the nephelometric measurement, this suspension was diluted to 0.065 g/l solids and treated with ultrasound. A standard serum containing 70 IU/ml rheumatoid factors was used, and the standard series automatically diluted 1:2.5 to 160 in the apparatus, i.e. RF concentrations of 28 IU, 14, 7, ... 0.45 IU/ml were obtained. The sera to be determined were diluted in a phosphate-sodium chloride buffer solution. For the measurement, 30 μl of a dilution of patient's serum and 40 μl of the latex-immune complex reagent were used. The measurement took place after 6 min at room temperature in a nephelometer (BNA, Behringwerke AG, Marburg). The standard curve for the measurement of the standard serum was plotted and the values measured for the patient's sera were evaluated from it.

Sera with known RF concentrations were tested. At a serum dilution of 1:20, the measurement range was from 18 to 560 IU/ml (normal range: ≦20 IU RF/ml).

C) Latex-immune complex reagent was employed for measuring rheumatoid factors in patient's sera. The RF standard contained 70 IU RF/ml. The standard was diluted stepwise in the nephelometer with phosphate- sodium chloride buffer. A standard series was thus obtained with decreasing RF concentrations.

The patient's sera to be determined were diluted in phosphate-sodium chloride buffer. For the measurement 30 μl of a dilution of the patient's serum, or a dilution of the standard serum, were incubated for 6 min at room temperature with 40 μl of the latex-immune complex reagent and 30 μl of a reaction buffer solution which contained 1.2 g/100 ml NaCl, 1.3 g/100 ml $Na_2HPO_4$, 0.2 g/100 ml $Na_2PO_4$ and 5.6 g of polyethylene glycol 6000. The results were then measured in a nephelometer (Behringwerke AG, Marburg).

At a 1:20 serum dilution the measurement range was 9 to 560 IU/ml, and at a 1:100 serum dilution 45 to 7000 IU/ml.

|  | RF IU/ml Serum dilution | |
| --- | --- | --- |
| Serum No. | 1:20 | 1:100 |
| 1 | 393 | 401 |
| 2 | 328 | 326 |
| 3 | 181 | 180 |
| 4 | <9 | <45 |
| 5 | 195 | 186 |

Serum 4 was negative.

The table shows the very good recovery and dilution consistency in the determination of the rheumatoid factors according to the invention.

EXAMPLE 2

A) Coating the microtiter plates

An immune complex (prepared according to 1 A) was diluted in 0.05 mol/l sodium phosphate buffer, pH 6.6, to a concentration of 12 µg/ml. 135 µl of the dilution were dispensed into each well of a microtiter plate (e.g. from NUNC).

The plates were covered with film and incubated overnight at room temperature. Following incubation, the plates were in each case washed twice with 250 µl of 0.1 mol/l Tris-citrate buffer, pH 4.9, per well and air-dried.

B) Performance of the test

1) All the reagents and samples were warmed to +18 to +25° C. The samples were diluted 1:101 (10 µl +1 ml) in a protein-containing Tris buffer, pH 8.2, and mixed well.

2) In each case, 100 µl of the diluted samples, controls and standards were added per well, and the filled test plate was covered and incubated at +37° C (±1° C) for 60 min.

3) Subsequently the test plate was washed 4 times with on each occasion 0.3 ml of Tween-containing phosphate buffer solution.

4) Next, 100 µl of anti-human IgM/POD-conjugate were added per well, and the plate was then incubated at +37° C for 60 min and washed as under paragraph 3.

5) 100 µl of chromogen-buffer/substrate solution (tetramethylbenzidine dihydrochloride in a hydrogen peroxide-containing acetate buffer solution) were added to each well, and the plate was covered and incubated at +20 to +25° C for 30 min while being protected from light. After adding 100 µl of stop solution (0.5 N sulfuric acid) per well, the plate was read photo- metrically at 450 nm measurement wavelength and 650 nm reference wavelength. Evaluation of the test was achieved with the aid of a standard curve (polygonal interpolation) using the extinction values of the standards.

The following table shows a comparison of RF values, which were determined using the immune complex ELISA and using a quantitative RF test according to the present state of the art:

| Serum No. | ELISA RF/IgM (IU/ml) | Nephelometric RF determination (IU/ml) |
| --- | --- | --- |
| 1 | 236 | 228 |
| 2 | 65 | 84 |
| 3 | 101 | 104 |
| 4 | 42 | 52 |
| 5 | 62 | 60 |
| 6 | 16 | 21 |

The invention claimed is:

1. A process for preparing a diagnostic reagent for Rheumatoid Factor which comprises the steps of:
    a) preparing soluble immune complexes having which an antigen portion and an antibody portion by mixing an antigen and a corresponding antibody elicited by the antigen in an aqueous solution;
    b) incubating said immune complex resulting from step a) with a suspension of latex particles, wherein a portion of the immune complexes attach to the latex particles by the antigen portion of the immune complex, and a portion of the immune complexes attach to the latex particles by the antibody portion of the immune complex;
    c) recovering particles coated with said immune complex from suspension, and
    d) resuspending particles coated with said immune complex in a storage-stable medium.

2. The process of claim 1, wherein the immune complex has been prepared rom antibody from animals immunized with an antigen of human, animal or vegetable origin, wherein said antigen is not Rheumatoid Factor.

3. The process of claim 1, wherein the molar ratio antibody:antigen in the immune complex is 1:0.05 to 5.

4. The process as claimed in claim 1, wherein the antibody is from a mammal selected from the group consisting of sheep and rabbit.

5. The process of claim 1, wherein the immune complex is prepared in an aqueous solution in the presence of up to 50% by volume of a cyclic amide.

6. The process as claimed in claim 1, wherein the antibody is a monoclonal antibody.

7. The process of claim 1 wherein the aqueous solution contains a polar solvent readily miscible in water.

8. The process of claim 7 wherein the polar solvent readily miscible in water is dimethyl sulfoxide or dimethylformamide.

9. The process of claim 7 wherein the polar solvent readily miscible in water is pyrrolidone.

10. A diagnostic kit comprising the diagnostic reagent prepared by the process of claim 1 and a positive control solution containing Rheumatoid Factor.

11. A diagnostic reagent for the detection of Rheumatoid Factor produced by the process of claim 1.

12. A diagnostic method for the detection and determination of Rheumatoid Factor in a sample of a biological fluid which comprises the steps of
    a) incubating the sample with the diagnostic reagent of claim 11;
    b) allowing the coated particles to react with Rheumatoid Factor in the sample; and
    c) detecting the degree of agglutination of the particles caused by Rheumatoid Factor present in the sample; and
    d) determining the Rheumatoid Factor in said sample based on the degree of agglutination in step c).

13. The method of claim 12, wherein the detection in step c) is selected from the group consisting of visual detection, nephelometric detection, and turbidimetric detection.

14. A diagnostic reagent for the detection of Rheumatoid Factor comprising a suspension of latex-particles having immune- complexes absorptively immobilized thereon in a storage-stable medium, wherein the immune-complexes have been preformed from IgG and anti-IgG before absorption and wherein the IgG/anti-IgG complexes bind to Rheumatoid Factor.

15. A diagnostic kit comprising the diagnostic reagent of claim 14 and at least one solution containing Rheumatoid Factor in a known amount.

* * * * *

UNITED STATES PATENT AND TRADEMARK OFFICE
CERTIFICATE OF CORRECTION

PATENT NO. : 5,989,922
DATED : November 23, 1999
INVENTOR(S) : Tibor Toth

It is certified that error appears in the above-identified patent and that said Letters Patent is hereby corrected as shown below:

In Claim 1, col. 5, line 62, "complex" should read --complexes--.

In Claim 1, col. 6, line 5, "said immune complex" should read --the immune complexes--.

In Claim 1, col. 6, lines 7-8, "said immune complex" should read --the immune complexes--.

In Claim 2, col. 6, line 11, "rom" should read --from--.

In Claim 9, col. 6, line 31, after "pyrrolidone", insert --($\gamma$-aminobutyrolactam)--.

In Claim 14, col. 6, line 55, "immune- complexes" should read --immune-complexes--.

Signed and Sealed this

Sixth Day of February, 2001

Attest:

Q. TODD DICKINSON

Attesting Officer

Director of Patents and Trademarks